(12) United States Patent
Shim et al.

(10) Patent No.: US 9,175,344 B2
(45) Date of Patent: Nov. 3, 2015

(54) STRUCTURE WITH NANOPORE AND APPARATUS FOR DETERMINING SEQUENCES OF NUCLEIC ACIDS INCLUDING THE SAME

(75) Inventors: Bongchu Shim, Seoul (KR); Dami Kim, Seoul (KR); Seongmoon Cho, Seoul (KR); Jeankun Oh, Seoul (KR)

(73) Assignee: LG ELECTRONIC INC., Seoul (KR)

( * ) Notice: Subject to any disclaimer, the term of this patent is extended or adjusted under 35 U.S.C. 154(b) by 308 days.

(21) Appl. No.: 13/878,091

(22) PCT Filed: Oct. 31, 2011

(86) PCT No.: PCT/KR2011/008206
§ 371 (c)(1),
(2), (4) Date: Apr. 5, 2013

(87) PCT Pub. No.: WO2012/060595
PCT Pub. Date: May 10, 2012

(65) Prior Publication Data
US 2013/0203608 A1    Aug. 8, 2013

(30) Foreign Application Priority Data

Nov. 1, 2010  (KR) .................. 10-2010-0107812

(51) Int. Cl.
*C12Q 1/68*  (2006.01)

(52) U.S. Cl.
CPC ............ *C12Q 1/6874* (2013.01); *C12Q 1/6869* (2013.01)

(58) Field of Classification Search
CPC .................. C12Q 2565/631; C12Q 2565/632; C12Q 1/6869
See application file for complete search history.

(56) References Cited

U.S. PATENT DOCUMENTS

| 6,652,808 B1 * | 11/2003 | Heller et al. ................. 422/68.1 |
| 2005/0192438 A1 | 9/2005 | Shenoy et al. |
| 2008/0254995 A1 | 10/2008 | Kim et al. |
| 2009/0298072 A1 | 12/2009 | Ju |

FOREIGN PATENT DOCUMENTS

WO    WO 2010/117470 A2    10/2010

OTHER PUBLICATIONS

Branton et al., "The potential and challenges of nanopore sequencing," Nature Biotechnology, vol. 26, No. 10, Oct. 2008, pp. 1146-1153.
Derrington et al., "Nanopore DNA sequencing with MspA," PNAS, vol. 107, No. 37, Sep. 14, 2010, pp. 16060-16065.
Gupta, "Single-molecule DNA sequencing technologies for future genomics research," Trends in Biotechnology, vol. 26, No. 11, Aug. 21, 2008, pp. 602-611.

* cited by examiner

*Primary Examiner* — Samuel Woolwine
(74) *Attorney, Agent, or Firm* — Birch, Stewart, Kolasch & Birch, LLP

(57) ABSTRACT

Disclosed are a structure with a nanopore and an apparatus for determining sequences of nucleic acids including the structure, the structure including three or more structures having facing surfaces, a plurality of oligonucleotides attached at one ends thereof to the surfaces, and a pore formed between the structures to which the plurality of oligonucleotides are bound, and allowing a pore of a desired size to be precisely formed by adjusting the length of a plurality of oligonucleotides.

10 Claims, 4 Drawing Sheets

STRUCTURE WITH NANOPORE AND APPARATUS FOR DETERMINING SEQUENCES OF NUCLEIC ACIDS INCLUDING THE SAME

TECHNICAL FIELD

The present invention relates generally to a method for forming a pore for detecting or analyzing a target substance present in a sample and a structure with the pore and, more particularly, to a method and structure capable of adjusting a size of a pore as desired and an apparatus for determining sequences of nucleic acids including the structure.

BACKGROUND ART

Various methods have been developed to detect a target biomolecule in a specimen. Among them, a method using a nanopore is similar to a bio-pore system and has appealed to those skilled in the art as a high-sensitivity DNA detection system.

There are known various DNA detection systems using nanopores. One example of the detection systems is found in U.S. Pat. No. 6,015,714, which is entitled "characterization of individual polymer molecules based on monomer-interface interactions" and is intended to distinguish respective bases constituting DNA from each other using a very sensitive signal of a nanopore, thus performing DNA sequencing. According to the cited document, this has two pools, with a small pore being formed between the pools to permit DNA to enter one by one. After a DNA biopolymer is loaded on either of the pools, the passage of the biopolymer through the pore is measured, thus performing the DNA sequencing.

Further, U.S. Pat. No. 6,362,002, entitled "characterization of individual polymer molecules based on monomer-interface interactions", discloses a method for making a nanopore to allow bases of a single stranded DNA to sequentially pass and determining a double stranded nucleic acid and a single stranded nucleic acid. Here, since the double stranded nucleic acid is untwisted in a single strand prior to passage, a long time is required.

Furthermore, U.S. Pat. Appl. Publication No. 2003/0104428, entitled "a method for characterization of nucleic acid molecules", discloses technology that identifies a specific sequence using substances recognizing a specified local area of DNA, for example, protein or DNA and observes a signal variation caused by other substances bound to DNA so as to determine characteristics of a DNA sample using a nanopore, thus detecting a specific DNA sequence.

U.S. Pat. No. 6,428,959, entitled "methods of determining the presence of double stranded nucleic acids in a sample", discloses a method that measures amplitude of current flowing through a nanopore while nucleic acids in a fluid specimen pass through the nanopore having a diameter of 3 nm to 6 nm, thus distinguishing a double stranded nucleic acid from a single stranded nucleic acid by current blockade.

However, the conventional DNA detection method and apparatus using the nanopore is problematic in that a diameter of the nanopore is large to deteriorate resolution where a required diameter of nanopore should be less than 10 nm, preferably 5 nm, so that the structure and detection conditions for the DNA detection apparatus are very complicated.

Until now, many efforts have been made to form a nanopore of a small diameter like a bio-pore. However, there are practically many problems because of manufacturing difficulties.

DISCLOSURE OF INVENTION

Technical Problem

Accordingly, the present invention has been made keeping in mind the above problems occurring in the prior art, and an object of the present invention is to simply and easily form a pore of a desired size.

Another object of the present invention is to provide a structure with a nanopore and an apparatus for determining sequences of nucleic acids.

Solution to Problem

In one aspect of the present invention, there is provided a structure with a nanopore, comprising three or more structures having facing surfaces; a plurality of oligonucleotides attached at one ends thereof to the surfaces; and a pore formed between the structures to which the plurality of oligonucleotides are bound.

Preferably, the oligonucleotides attached to the facing surfaces may have complementary sequences.

A binding of the plurality of oligonucleotides may be performed such that the oligonucleotides attached to the surfaces of two of the structures having the facing surfaces are bound to each other.

Further, the oligonucleotides may comprise 2 to 100,000 oligonucleotides, and each of the oligonucleotides may have a length of 2 to 300 bp.

More preferably, the pore may be formed in a space where the three or more structures are adjacently situated.

In another aspect of the present invention, there is provided an apparatus for determining sequences of nucleic acids, comprising a structure with a nanopore including three or more structures having facing surfaces; a plurality of oligonucleotides attached at one ends thereof to the surfaces; and a pore formed between the structures to which the plurality of oligonucleotides are bound; an electrode provided on another surface adjacent to the facing surfaces; and a tip connected to the electrode, and located in the pore.

Preferably, the tip is located in a space where the three or more structures are adjacently situated.

The facing surfaces may be side surfaces of the three or more structures, and the another surface adjacent to the facing surfaces may be a front surface or a rear surface of each of the three or more structures.

Further, the tip may be formed at a vertex of the another surface adjacent to the facing surfaces. The vertex may be a point of intersection between the facing surfaces and the another surface adjacent thereto.

Preferably, tips may be so arranged as to face each other.

The apparatus may further include a laser generator for irradiating a laser beam to the pore, and a detector for receiving a laser signal from the pore.

In still another aspect of the present invention, there is provided a method for forming a nanopore, comprising steps of preparing three or more structures having facing surfaces; attaching one ends of a plurality of oligonucleotides to the facing surfaces; and binding the plurality of oligonucleotides to each other, wherein the oligonucleotides attached to the facing surfaces have complementary sequences.

The present invention may provide a method for manufacturing the structure with the nanopore which further includes a step of forming a pore between the structures by the binding of the oligonucleotides.

The present invention may provide a method for manufacturing an apparatus for determining sequences of nucleic acids, wherein each of the structures comprises an electrode provided on another surface adjacent to the facing surfaces, and a tip connected to the electrode and located in a space where the three or more structures are adjacent to each other.

The present invention may provide a method for determining sequences of nucleic acids, which further includes a step of receiving a current variation signal from the electrode.

The present invention may provide a method for determining methylation of sequences of nucleic acids, which further includes a step of irradiating a laser beam to the pore and receiving a laser signal from the pore.

The above and other objects, features and advantages of the present invention will be more clearly understood from the following detailed description taken in conjunction with the accompanying drawings.

Advantageous Effects of Invention

As apparent from the above description, the present invention is advantageous in that a pore of a desired size can be precisely formed by adjusting the length of a plurality of oligonucleotides attached to a surface of a structure. According to the prior art, it is impossible to manufacture a nanopore having a diameter of 10 nm or less. However, according to the present invention, a nanopore can be manufactured to have a diameter less than 10 nm, preferably 5 nm, more preferably 1 nm.

Further, the present invention is advantageous in that a plurality of oligonucleotides is attached to surfaces of structures and then the structures are combined with each other, thus allowing a nanopore to be formed simply and easily.

Furthermore, the present invention is advantageous in that sequences of nucleic acids can be directly determined by a nanopore without amplification or synthesis of nucleic acids, so that cost and time required for whole genome sequencing can be considerably reduced, and besides, methylation in the sequences of nucleic acids can be checked.

BEST MODE FOR CARRYING OUT THE INVENTION

Figure 1:
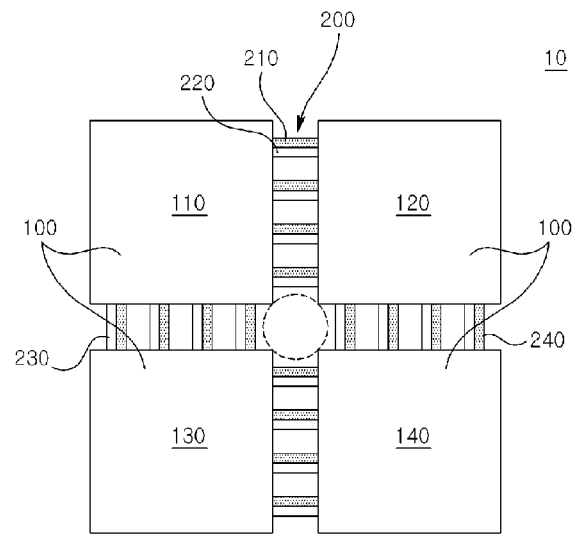
FIG. 1 is a front view illustrating a structure with a nanopore according to an embodiment of the present invention.

Since the present invention may be variously changed and include several embodiments, particular embodiments shown in the drawings will be described in detail in a detailed description. However, it is to be understood that the present invention is not limited to the particular embodiments, and various changes, equivalences and substitutions may be made without departing from the scope and spirit of the invention. When it is determined that the detailed description of the known art related to the present invention may obscure the gist of the present invention, the detailed description will be omitted.

Also it is to be understood that terms employed herein are for the purpose of description of particular embodiments and not of limitation. Further, the singular forms include plural referents unless the context clearly dictates otherwise. Further, it should be understood that terms "include" or "have" are inclusive of characteristics, numerals, steps, operations, components, parts or combinations thereof, bur are not exclusive of one or more different characteristics, numerals, steps, operations, components, parts or combination thereof.

Although the terms "first", "second", etc. are used herein to describe various components, these components should not be limited by these terms. These terms are only to distinguish one component from another component.

Figure 2:
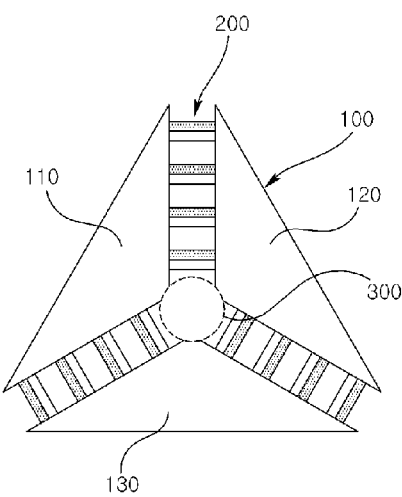
FIG. 2 is a front view illustrating a structure with a nanopore comprising three structures according to an embodiment of the present invention.
Figure 3:
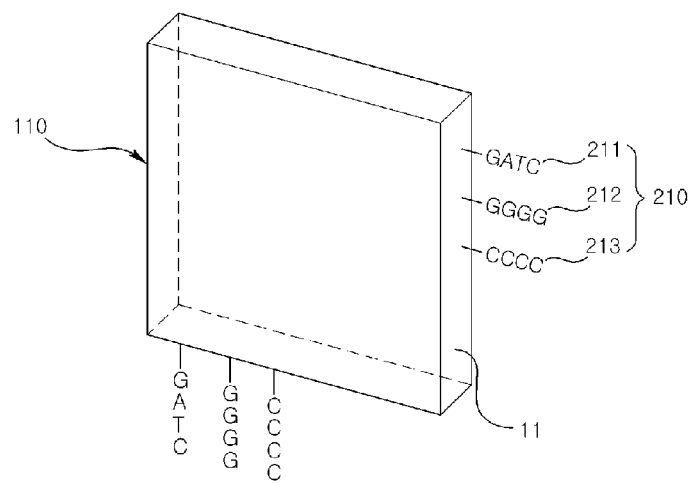
FIG. 3 is a perspective view illustrating an example wherein a plurality of oligonucleotides is attached to a first structure according to the present invention.
Figure 4:
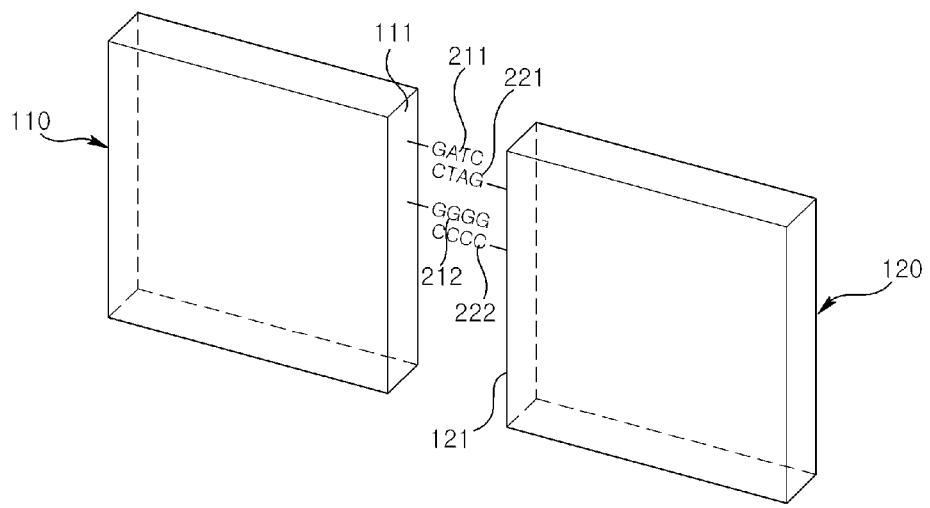
FIG. 4 is a perspective view illustrating an example wherein first and second structures according to the present invention are combined with each other.
Figure 5:
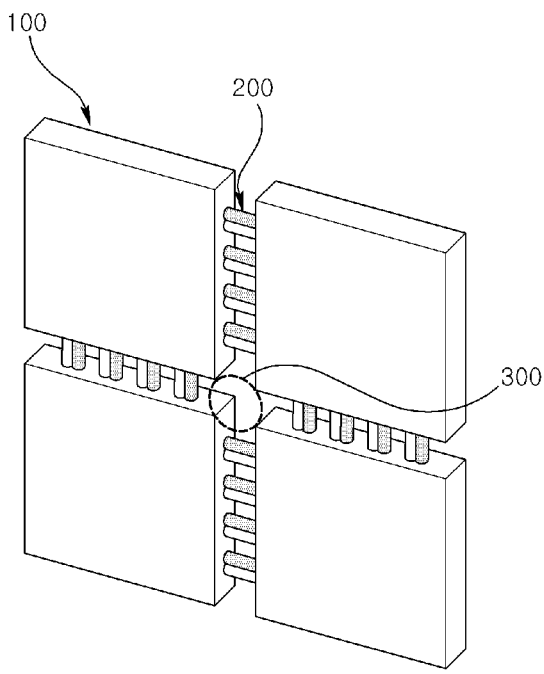
FIG. 5 is a perspective view illustrating the structure with the nanopore according to the embodiment of the present invention.

FIG. 1 is a front view illustrating a structure with a nanopore according to an embodiment of the present invention, FIG. 2 is a front view illustrating a structure with a nanopore comprising three structures according to an embodiment of the present invention, FIG. 3 is a perspective view illustrating an example wherein a plurality of oligonucleotides is attached to a first structure according to the present invention, FIG. 4 is a perspective view illustrating an example wherein first and second structures according to the present invention are combined with each other, and FIG. 5 is a perspective view illustrating the structure with the nanopore according to the embodiment of the present invention.

As shown in the drawings, a structure 10 with a nanopore according to the present invention includes three or more structures 100, a plurality of oligonucleotides 200, and a pore 300.

The structure 100 comprises three or more structures, for example, a first structure 110, a second structure 120 and a third structure 130. Further, the structure 100 may comprise a first structure 110, a second structure 120, a third structure 130 and a fourth structure 140. The structure 100 defines a body of the present invention. Preferably, as shown in FIG. 1, the first, second, third, and fourth structures 110, 120, 130 and 140 are located to be adjacent to each other, thus defining the body of the apparatus for determining sequences of nucleic acids according to the present invention.

The structure 100 may be accommodated in one chamber of the sequence determining apparatus, may be an interface for separating two chambers from each other or a structure having the interface. That is, in a vessel or well containing a sample and a reaction solution, the structure 100 may be one membrane or wall for separating or dividing the vessel or well. As will be described below, the pore between the structures may form a channel for connecting separated or divided spaces to each other.

The structure 100 may have various shapes known to those skilled in the art, without being limited to a specific shape. That is, each of the first, second, third, and fourth structures 110, 120, 130 and 140 may take a shape of a polyhedron, for example, a cuboid whose side is a rectangular as shown in FIG. 1. Further, each of the first, second and third structures 110, 120 and 130 may take a shape of a pentahedron whose side is a triangle as shown in FIG. 2. Unit blocks constituting the structure 100 are not limited to a specific shape and number. Preferably, the structure 100 may comprise 3 to 12 unit blocks. The present invention is characterized in that three or more structures 100 are connected to each other and thus the pore is formed in a space adjacent to the structures. It is preferable that the structure 100 comprise three or more blocks. It is impossible for only two blocks to form a pore in the space adjacent to the structures.

The structure 100 covers all materials and components known to those skilled in the art, without being limited to a specific material or component. For example, each of the first, second, third and fourth structures 110, 120, 130 and 140 may be a substrate comprising Si, Ge, GaAs, AlAs, AlSb, GaN, GaP, GaSb, InP, Al2O3, SiC, InSb, CdSe, CdS, CdTe, InAs, ZnTe, ZnO or ZnS. Unlike this example, each of the first, second, third and fourth structures 110, 120, 130 and 140 may be a substrate comprising organic matter, PVK (poly(N-vinylcabazole)), MEH-PPV (poly(2-methoxy-5-(2'-ethylhexyloxy)-p-phenylene vinylene), n-type fullerene, poly-acetylene, polythiophene, phthalocyanine, poly(3-hexylthiophene), poly(3-alkylthiophene), α-ω-hexathiophene, α-ω-di-hexyl-hexathiophene, poly-thienylenevinylene, or Bis(dithienothiophene).

Further, the respective structures 100 have facing surfaces. That is, each of the first, second, third and fourth structures 110, 120, 130 and 140 has a surface that faces a neighboring structure. For example, as shown in FIG. 1, the first and fourth structures 110 and 140 have surfaces that face the second and third structures 120 and 130. As shown in FIG. 4, the first and second structures 110 and 120 may have facing surfaces 111 and 121, respectively.

The present invention is characterized in that oligonucleotides are attached to the facing surfaces 111 and 121 of the three or more structures 100 and then the structures 100 are combined with each other. To this end, it is preferable that each of the facing surfaces 111 and 121 of the structures 100 be wholly or partially used for attachment of oligonucleotides or nucleotides of polynucleotides.

The facing surfaces 111 and 121 may comprise gold or a gold layer formed on silicon nitride membrane. Further, the facing surfaces 111 and 121 may be preferably formed such that nucleotides are bound to SiO2, Al2O3, TiO2, BaTiO3, PbTiO3, or Si3N4 membrane. To this end, surface modification is performed to have a carboxyl group (—COOH), a thiol group (—SH), a hydroxyl group (—OH), a silane group, an amine group or an epoxy group using a conventional method known in a DNA or protein chip. Each of the facing surfaces 111 and 121 may have a thickness of 100 to 500 nm. Each of the facing surfaces 111 and 121 may be formed on a surface of the structure 100 by pulsed laser deposition, sputtering, chemical vapor deposition, e-beam evaporation, thermal evaporation, etc.

The plurality of oligonucleotides 200 are attached at one ends thereof to the facing surfaces of the structures 100. That is, one end of each oligonucleotide 200 is attached to one of the facing surfaces of the first, second, third, and fourth structures 110, 120, 130 and 140.

The plurality of oligonucleotides 200 comprise a first oligonucleotide 210 attached to a surface of the first structure 110, a second oligonucleotide 220 attached to a surface of the second structure 120, a third oligonucleotide attached to a surface of the third structure 130, and a fourth oligonucleotide attached to a surface of the fourth structure 140.

For example, as shown in FIG. 3, a plurality of first oligonucleotides 210 may be attached to a surface 111 of the first structure 110 that faces a surface of the second structure 120, as well as a surface of the first structure 110 that faces a surface of the third structure 130. Further, as shown in FIGS. 1 and 4, a plurality of second oligonucleotides 220 may be attached to a surface 121 of the second structure 120 that faces a surface of the first structure 110, as well as a surface of the second structure 120 that faces a surface of the fourth structure 140.

It is preferable that the first and second oligonucleotides 210 and 220 attached to the facing surfaces 111 and 121 have complementary sequences. That is, the plurality of complementary oligonucleotides 200 are attached to the facing surfaces of the first and second structures 110 and 120. Thus, by binding the oligonucleotides 200 together, the structures 100 comprising the first and second structures 110 and 120 are combined with each other.

For example, as shown in FIGS. 3 and 4, the first oligonucleotides 210 may be composed of different bases or the same base. That is, oligonucleotides 211, 212 and 213 constituting the first oligonucleotides 210 may comprise the same base or combination of different bases. Further, each first oligonucleotide 211, 212 or 213 may comprise the same base sequence or different base sequences. The oligonucleotides 211, 212 and 213 attached to the surface 111 of the first structure 110 and the oligonucleotides 221, 222 and 223 attached to the surface 121 of the second structure 120 facing the surface 111 may complementary to each other in all or some bases.

If all of the first oligonucleotides 210 attached to one structure 100 preferably have the same base, the first oligonucleotides 211, 212 and 213 are not bound to each other, thus enhancing binding between the first oligonucleotides 210 and the second oligonucleotides 220 attached to the facing surface of the second structure 200.

According to the present invention, it is more preferable that the plurality of oligonucleotides 200 have the same length. By adjusting the length, it is possible to precisely form a pore of a desired size.

For example, it is desirable that the plurality of first oligonucleotides 210 attached to the first structure 110 and the plurality of second oligonucleotides 220 attached to the second structure 120 be located at corresponding positions. That is, in order to conform to the sequence of the first oligonucleotides 210 attached to the surface 111 of the first structure 110, the second oligonucleotides 220 complementary to the first oligonucleotides 210 are attached to the surface 121 of the second structure 120 in sequence. More preferably, the first and second oligonucleotides 210 and 220 are arranged in a row in sequence, but may be variously arranged in an "S" shape, a zigzag shape, etc. As long as the first and second oligonucleotides 210 and 220 have complementary bases to be bound together, the oligonucleotides may be arranged in two or more layers on the facing surfaces 111 and 121 to increase a coupling force between the structures 100.

The first oligonucleotides 210 may be attached, each spaced apart from the other, by a predetermined distance, or may be compactly attached such that side surfaces thereof are in close contact with each other (in this case, a binding may be performed using other surfaces of the first oligonucleotides 210 which are not in close contact with each other, namely, in a vertical direction of FIG. 1). After the first oligonucleotides 211, 212 and 213 are bound at side surfaces to form a set, the set may be attached to the surface of the structure.

A method for attaching ends of the plurality of oligonucleotides 200 to the surface of the structure 100 is not limited to a specific method, but may use a conventional method known in a DNA or protein chip. To this end, it is preferable that a specific functional group be previously embedded at a specific position on the surface of the structure 100 for the attachment of nucleotide. For example, a reactive group selected from a group comprising aldehyde, carboxyl, ester, activated ester, amino and combinations thereof is applied to an end of each oligonucleotide 200, so that it may be fixed to a surface of the structure 100 via the reactive group.

Preferably, the number of the oligonucleotides 200 attached to a surface is 2 to 100,000. If the number of the oligonucleotides is less than 2, a coupling force between the structures 100 is too weak. Meanwhile, if the number of the oligonucleotides exceeds 100,000, it is technically difficult to attach the oligonucleotides 200 to the predetermined surface, and besides, oligonucleotides attached to the same surface may be undesirably bounded to each other.

Further, it is preferable that each oligonucleotide 200 have a length of 2 to 300 bp. As well known to those skilled in the art, the distance of 1 bp in the oligonucleotide is equal to about 0.34 nm. Thus, if the single-stranded oligonucleotide of 10 bp is used for example, a distance between the structures 100 may be 3.4 nm. As such, a nanopore of a desired size can be formed by adjusting the length of the oligonucleotide.

The pore 300 is formed between the structures 100 to which the oligonucleotides 200 are bound.

That is, the plurality of oligonucleotides 210 and 220 attached to the facing surfaces 111 and 121 of the two structures 110 and 120 among the structures 100 have complementary regions. If the first, second, third, and fourth structures 110, 120, 130 and 140 approach each other, they may be naturally hybridized, so that the first, second, third and fourth structures 110, 120, 130 and 140 may form a physical structural coupling.

Such a coupling provides a barrier or an interface between the first, second, third, and fourth structures 110, 120, 130 and 140 to prevent passage of target nucleic acid molecules, and defines the pore 300 or the channel in a central space between the first, second, third and fourth structures 110, 120, 130 and 140 to permit passage of target nucleic acid molecules. That is, the pore 300 may be formed in the central space between the adjacent first, second, third and fourth structures 110, 120, 130 and 140.

Therefore, according to the present invention, a pore of a desired size can be precisely formed by adjusting the length of a plurality of oligonucleotides attached to the surface of the structure. According to the prior art, it is impossible to manufacture a nanopore having a diameter of 10 nm or less. However, according to the present invention, it is possible to manufacture a nanopore having a diameter less than 10 nm, preferably 5 nm, and more preferably 1 nm, thus providing a detection apparatus having excellent resolution.

Further, the present invention may provide an apparatus for detecting target nucleic acid molecules using a nanopore, which includes the structure 10 with nanopore, an electrode for applying voltage to the pore 300 of the structure 10, and a measuring unit for measuring an electric signal generated when DNA or a specimen having the DNA passes through the pore 300.

It is preferable that the pore used in the apparatus of the present invention be a channel or hole whose diameter is a nanometer size. The apparatus and method for detecting nucleic acid molecules using the nanopore according to the present invention remain the same as the prior art except for the above-mentioned structure 10 with the nanopore.

This invention has been described herein with reference to oligonucleotides. However, it is apparent to those of ordinary skill in the art that the present invention is characterized by the binding between complementary nucleotides, so that the use of polynucleotides also falls with the purview of the present invention.

Mode for the Invention

Figure 6:
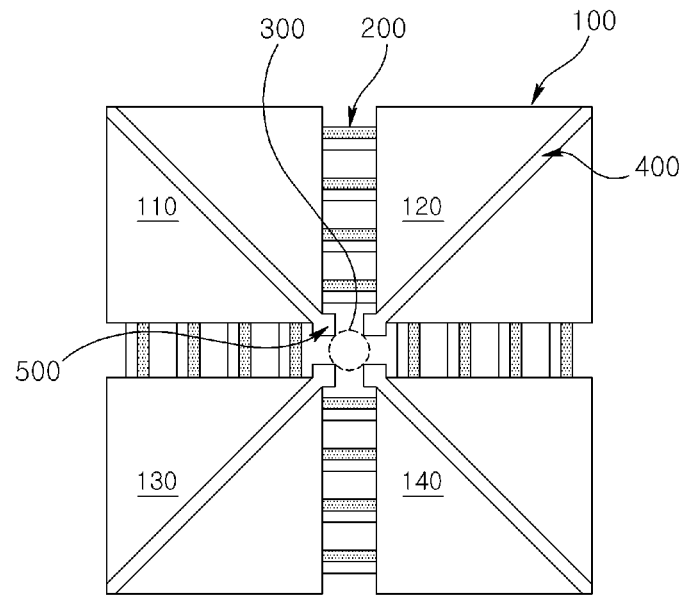
FIG. 6 is a front view illustrating an apparatus for determining sequences of nucleic acids according to an embodiment of the present invention.
Figure 7:
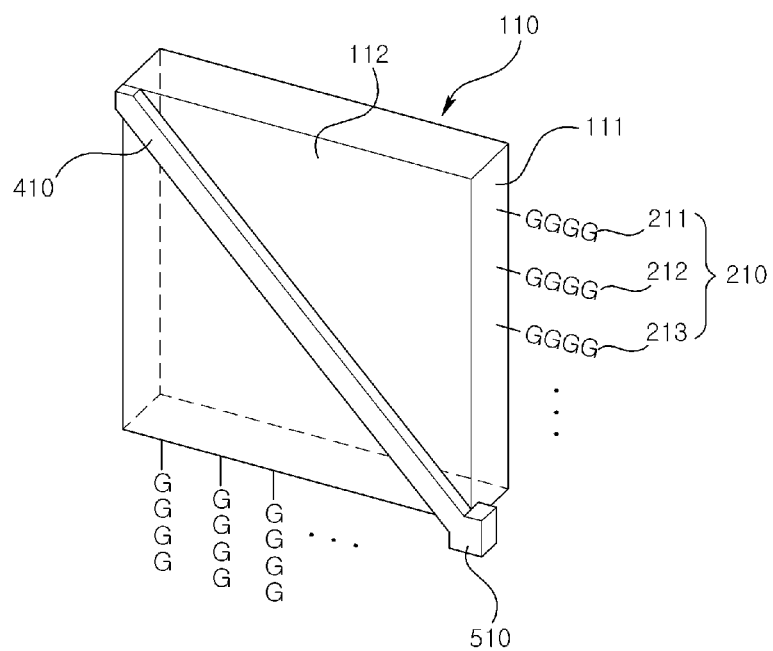
FIG. 7 is a perspective view illustrating an example wherein an electrode and a tip are formed on the first structure according to the present invention.
Figure 8:
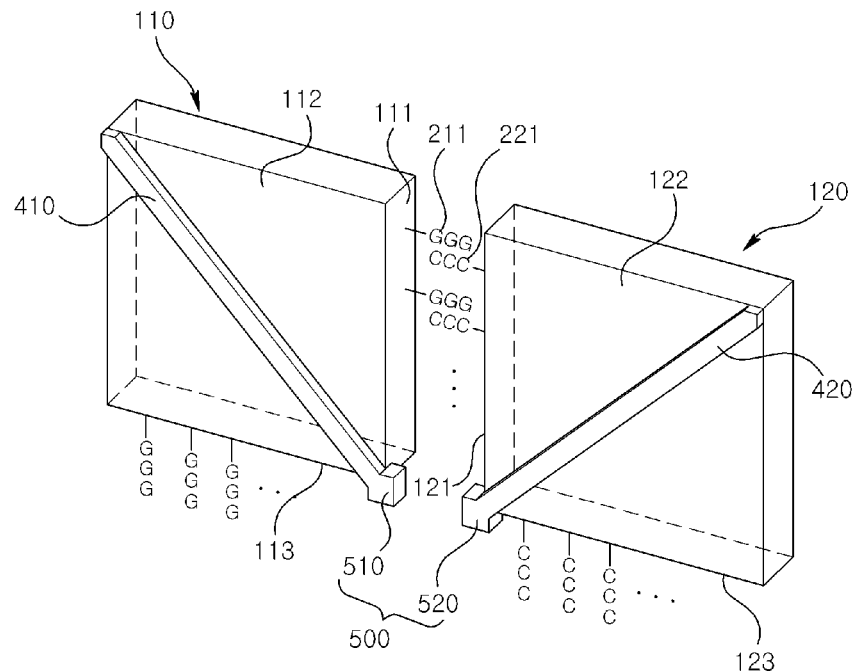
FIG. 8 is a perspective view illustrating an example wherein the first and second structures each having an electrode and a tip according to the present invention are combined with each other.
Figure 9:
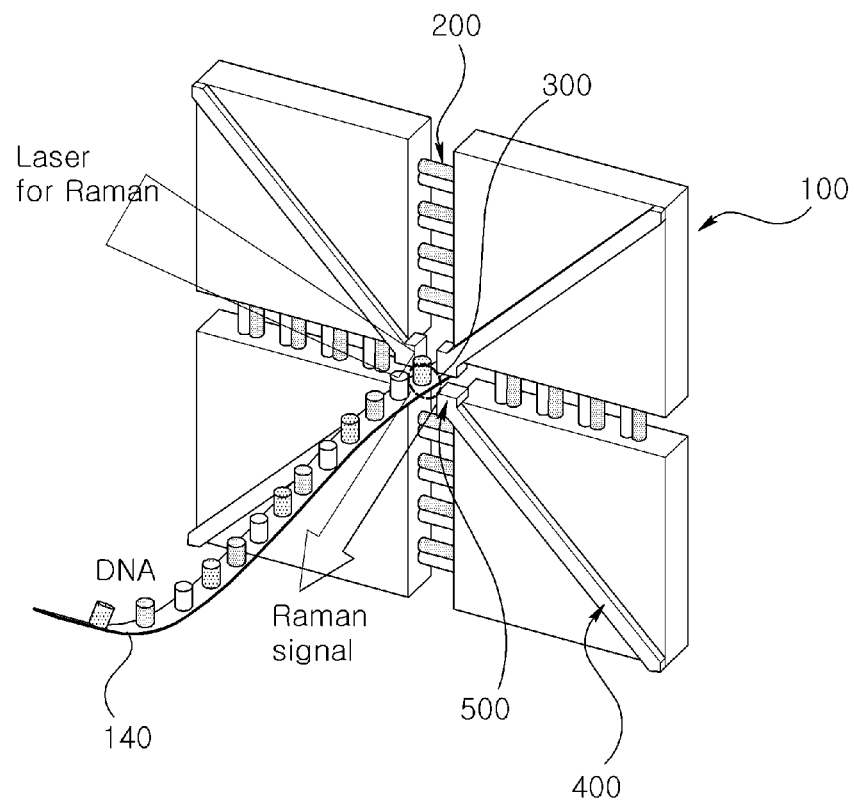
FIG. 9 is a perspective view illustrating the apparatus for determining sequences of nucleic acids according to the embodiment of the present invention.

FIG. 6 is a front view illustrating an apparatus for determining sequences of nucleic acids according to an embodiment of the present invention, FIG. 7 is a perspective view illustrating an example wherein an electrode and a tip are formed on the first structure according to the present invention, FIG. 8 is a perspective view illustrating an example wherein the first and second structures each having an electrode and a tip according to the present invention are combined with each other, and FIG. 9 is a perspective view illustrating the apparatus for determining sequences of nucleic acids according to the embodiment of the present invention.

Referring to the drawings, another embodiment of the present invention provides an apparatus for determining sequences of nucleic acids, including a structure 10 with a nanopore, an electrode 400, and a tip 500.

As described above, the structure 10 with the nanopore comprises three or more structures 100 having facing surfaces, a plurality of oligonucleotides 200 attached at one ends thereof to the surfaces, and a pore 300 formed between the structures 100 to which the plurality of oligonucleotides are bound.

Preferably, the three or more structures 100 are made of a non-conductive material to allow current to flow only in the electrodes 400 formed thereon. For example, the non-conductive material may be selected from a group comprising glass, ceramic, silicon, polystyrene, polyethylene, polypropylene, polyacrylamide and combinations thereof, but is not limited thereto.

It is preferable that the electrode 400 be provided on another surface adjacent to the facing surfaces of the structures 100. That is, the electrode 400 is attached to a surface different from the surfaces to which the oligonucleotides 200 are attached.

For example, as shown in FIGS. 7 and 8, when the facing surfaces 111 and 121 to which the oligonucleotides 200 are attached form side surfaces of three or more structures 100, another surface 112 adjacent to the facing surfaces 111 and 121 may be a front or back surface of each of the three or more structures.

The electrode 400 comprises a first electrode 410 formed on the first structure 110, a second electrode 420 formed on the second structure 120, a third electrode formed on the third structure 130, and a fourth electrode formed on the fourth structure 140.

Further, each electrode 400 is preferably formed on the surface of the structure 100 such that an end thereof is oriented towards a space in which the structures 100 are adjacent to each other. For example, as shown in FIG. 7, the first electrode 410 may be provided on a surface of the first structure 110 in such a way as to extend long in a diagonal direction thereof. Preferably, an end of the first electrode 410 is formed on a vertex of the front surface of the first structure 110, this vertex being located in the space in which the structures 100 are adjacent to each other. Such a configuration is suitable to obtain a current variation signal from the pore 300 formed in the space in which the structures 100 are adjacent to each other.

Such an electrode 400 is a part of the apparatus of the present invention in which current flows. For example, the electrode 400 may be made of a material selected from a group consisting of gold, platinum and indium tin oxide, but is not limited thereto.

According to an embodiment, the electrode 400 may be connected at an end thereof to a tip 500. That is, voltage is applied to the electrode 400 to supply current to the tip 500 connected to the end of each electrode 400. The supplied current varies as target nucleic acid molecules pass through the nanopore 300 formed in the apparatus of the present invention. Such a variation is converted into an electric signal to be detected by several electric detectors that are well known to those skilled in the art, such as a current measuring device.

The tip 500 is connected to the electrode 400, and is located in the space in which the pore 300 exists.

The tip 500 connected to the end of the electrode 400 may have various shapes without being limited to a specific shape. The tip 500 may have a straight line shape that is identical with that of the electrode 400. In this case, the electrode 400 protrudes to the space in which the pore 300 exists.

The tip 500 may be manufactured using etching technology known to those skilled in the art, for example, an AFM (Atomic Force MicroScopy) method. Further, the tip 500 may be made of a material selected from a group comprising gold, platinum, silver and copper, or this material may be deposited on the end of the electrode 400. For example, as shown in FIG. 8, the tip 500 may be formed on the vertex of another surface adjacent to the facing surfaces of the structures 100, that is, the front surface 112 of the first structure 110, the vertex being a portion at which the two facing surfaces 111 and 113 and another adjacent surface 112 meet commonly.

Such a tip 500 is an end at which current flowing through the electrode 400 arrives, and is located in the space having the pore 300. The tip 500 can more sensitively receive a variation in current using the target nucleic acid molecules passing through the pore 300.

Thereby, if the tip 500 is sharp at its end, it is preferable because the variation in current can be more excellently received. It is more preferable that the tip 500 be sharp at the end thereof while having a thickness or width greater than the electrode 400. It is the most preferable that the tip 500 take a shape of an arrow towards the pore.

Further, the tip 500 may define the pore 300 when the structures 100 are combined with each other to form the body of the apparatus according to the present invention. That is, the tip 500 may be located in the space where three or more structures 100 are adjacent to each other.

Thus, according to an embodiment of the present invention, tips 500 are arranged to face each other. The space formed by the tips 500 arranged in this way defines the pore 300. That is, in the apparatus of the present invention, the size of the pore 300 may be determined depending on a distance between the facing tips 500. For example, metal is deposited on an end of the electrode 400, thus forming the tip 500. The size of the pore 300 can be finely adjusted by adjusting the thickness of the deposited metal.

Therefore, the apparatus having the tips 500 can precisely form the pore 300 of a very small size and can adjust the size of the pore 300 in a simple and easy manner, as compared to an apparatus having no tip.

The apparatus for determining the sequences of nucleic acids according to the present invention may further include a laser generator for irradiating laser beams to the pore 300, and a detector for receiving a laser signal emitted from the pore 300.

The detector may be an optical detector an electric detector. The electric detector may detect at least one selected from a group including current, voltage, resistance and impedance, for example. The optical detector may detect at least one selected from a group including absorption, penetration, scattering, fluorescence, fluorescence resonance energy transfer (FRET), surface plasmon resonance, surface-enhanced Raman scattering and diffraction.

The apparatus of the present invention may further include a specimen storage chamber connected to the structure 100 to store a specimen that is put into the pore 300. The specimen is a PCR product, namely, a fluid substance including DNA amplified by a PCR method. Particularly, the DNA may be double- or single-stranded DNA having the size of 1 kbp or less. Further, the specimen storage chamber may be configured to store a specimen injected from an outside. Alternatively, the specimen storage chamber may be configured such that a desired specimen is generated using a known DNA amplification unit, e.g. a PCR chip and then is stored. If necessary, the specimen storage chamber may be configured such that it is connected to a DNA amplification unit connected to a fine channel having a nanopore-sized diameter and thus is supplied with a specimen containing DNA.

Moreover, although not described in detail herein, the respective functional components of the present invention may be implemented by a process-on-a-chip or a lab-on-a-chip using a known microfluidic unit and a MEMS device.

Meanwhile, another embodiment of the present invention provides a method for forming a nanopore. The method includes a step S100 of preparing three or more structures having facing surfaces, a step S200 of attaching one ends of a plurality of oligonucleotides to the facing surfaces, and a step S300 of binding the plurality of oligonucleotides to each other. The oligonucleotides attached to the facing surfaces have complementary sequences.

The three or more structures and the plurality of oligonucleotides remain the same as above described.

For example, a surface of silicon is cut to be sharp at an end, and silicon nitride, gold, and silicon nitride are sequentially deposited on a surface adjacent to the sharp vertex, so that a first structure block having on a side surface thereof a gold layer is prepared. In this way, second, third, and fourth structure blocks each having a gold layer are prepared.

Subsequently, the single-stranded DNA is attached to the gold layer on each of the facing surfaces of the first, second, third, and fourth structure blocks, and the first, second, third, and fourth structure blocks approach each other, so that the single-stranded DNA are bound together.

Thereby, such a binding allows the pore to be formed between the first, second, third and fourth structure blocks. The present invention may also provide a method for manufacturing the structure with the nanopore.

If the structure 100 includes the above-mentioned electrode 400 and tip 500, the present invention may provide a method for manufacturing an apparatus for determining sequences of nucleic acids.

The present invention may provide a method for determining sequences of nucleic acids, by adding a step S400 to the above nanopore forming method. At the step S400, a current variation signal is received from the electrode 400 after the target nucleic acid molecules pass through the pore 300.

For example, if the target nucleic acids pass through the pore 300 using the structure with the nanopore 10 manufactured by the above-mentioned manufacturing method, it is possible to detect and analyze the target nucleic acid molecules.

The DNA consists of four bases, adenin, guanin, cytosine, and thymine. The bases have different chemical configurations. Thus, when the single-stranded DNA passes through the pore 300, there occurs a difference in tunneling current between the bases. When the difference is detected as an electric signal and is changed into base information, it is possible to analyze the base sequence of desired DNA. To this end, the specimen containing the DNA passing through the pore 300 is dissolved in an electrically conductive solvent to be prepared as a fluid phase. In this case, any electrically conductive solvent may be used. The solvent is an aqueous solvent, may be pure water or water containing at least one additive, for example, buffer or salt (e.g. potassium chloride). The solvent is preferably ionized buffer solution such as 1M KCl or 10 Mm Tris-HCl. Further, the fluid specimen typically has pH of about 6.0 to 9.0.

Thus, the method for determining the sequences of nucleic acids according to the present invention applies an electric field through the pore 300, and monitors a variation in current through the pore 300, thus detecting the target substance in the fluid flowing through the pore 300. Since the amplitude of the current passing through the pore 300 is monitored during the flowing process of the fluid and the variation in amplitude relates to the passage of the target substance through the pore, the target substance can be efficiently detected based on the measured current amplitude value.

According to an embodiment, the present invention may provide a method for determining methylation of sequences of nucleic acids, which further includes a step S500 of irradiating laser beams to the pore 300 and receiving a laser signal emitted from the pore 300.

That is, if a laser generator and a Raman signal detector are mounted to the apparatus of the present invention and Raman spectroscopy is applied as shown in FIG. 9, SERS (Surface-Enhanced Raman Scattering) occurs, thus obtaining an amplified Raman signal. If a spectrum for a methyl group is analyzed based on the signal, it is determined whether a single-stranded DNA to be analyzed is methylated.

The invention claimed is:

1. An apparatus for determining sequences of nucleic acids, characterized by:
    a structure with a nanopore including three or more structures having facing surfaces;
    a plurality of oligonucleotides attached at one ends thereof to the surfaces; and
    a pore formed between the structures to which the plurality of oligonucleotides are bound;
    an electrode provided on another surface adjacent to the facing surfaces; and
    a tip connected to the electrode, and located in the pore.

2. The apparatus as set forth in claim 1, characterized in that the tip is located in a space where the three or more structures are adjacently situated.

3. The apparatus as set forth in claim 1, characterized in that the facing surfaces are side surfaces of the three or more structures, and the another surface adjacent to the facing surfaces is a front surface or a rear surface of each of the three or more structures.

4. The apparatus as set forth in claim 1, characterized in that the tip is formed at a vertex of the another surface adjacent to the facing surfaces.

5. The apparatus as set forth in claim 4, characterized in that the vertex is a point of intersection between the facing surfaces and the another surface adjacent thereto.

6. The apparatus as set forth in claim 1, characterized in that tips are so arranged as to face each other.

7. The apparatus as set forth in claim 1, further characterized by:
    a laser generator for irradiating a laser beam to the pore; and
    a detector for receiving a laser signal from the pore.

8. A method for manufacturing an apparatus for determining sequences of nucleic acids, the method comprising:
    preparing three or more structures having facing surfaces, an electrode provided on another surface adjacent to the facing surfaces, and a tip connected to the electrode wherein the tip is located in a space where the three or more structures are adjacent to each other;
    attaching one end of a plurality of oligonucleotides to the facing surfaces; and
    binding the plurality of oligonucleotides to each other, wherein the oligonucleotides attached to the facing surfaces have complementary sequences.

9. A method for determining sequences of nucleic acids by using the apparatus for determining sequence of nucleic acids according to claim 1, the method comprising:
    making the target nucleic acid molecules pass through the pore; and
    receiving a current variation signal from the electrode.

10. A method for determining methylation of sequences of nucleic acids by using the apparatus for determining sequences of nucleic acids according to claim 7, the method comprising:
    making the target nucleic acid molecules pass through the pore;
    irradiating a laser beam to the pore; and
    receiving a laser signal from the pore.

* * * * *